United States Patent [19]

Scurlock et al.

[11] 4,352,820

[45] Oct. 5, 1982

[54] METHOD FOR PROVIDING LONG-LASTING LOCAL ANESTHESIA AND COMPOUNDS AND COMPOSITIONS THEREFORE

[75] Inventors: James E. Scurlock; Benson M. Curtis, both of Seattle, Wash.

[73] Assignee: Virginia Mason Research Center, Seattle, Wash.

[21] Appl. No.: 215,223

[22] Filed: Dec. 11, 1980

[51] Int. Cl.³ .............................................. A61K 31/14
[52] U.S. Cl. .................................................... 424/329
[58] Field of Search ...................... 424/329; 260/567.6

[56] References Cited

PUBLICATIONS

C. Armstrong et al., J. of General Physiology, vol. 59, 1972, pp. 388–400.
Armstrong, J. of General Physiology, vol. 58, 1971, pp. 413–437.

Primary Examiner—Jerome D. Goldberg
Attorney, Agent, or Firm—George W. Neuner; David G. Conlin

[57] ABSTRACT

This disclosure describes a method for providing ultra-long local anesthetic effects. The method comprises administering an N,N,N-triethyl-N-alkyl ammonium salt wherein the alkyl group contains from 8 to 16 carbon atoms. The local anesthetic effect producing quaternary ammonium salts and pharmaceutical preparations containing such quaternary salts are also described.

8 Claims, 3 Drawing Figures

METHOD FOR PROVIDING LONG-LASTING LOCAL ANESTHESIA AND COMPOUNDS AND COMPOSITIONS THEREFORE

FIELD OF THE INVENTION

This invention relates to local anesthetics and particularly to ultra-long acting local anesthetics, to pharmaceutical preparations for providing local anesthesia, and to methods for treating acute and chronic pain using such local ultra-long acting anesthetics.

BACKGROUND OF THE INVENTION

Hundreds of local anesthetics have been synthesized and tested over the past century. Only a few, however, have proven to be clinically useful. Most of the drugs tested conformed to Lofgren's scheme. This scheme consists of an intermediate chain separating a lipophilic end from a hydrophobic end. The intermediate chain is typically 6 to 9 Å in length and contains a carbonyl group. These components have appeared to be essential to a clinically useful local anesthetic.

The few clinically useful local anesthetics have problems associated with them. Local anesthetics are still probably responsible for more deaths than any other class of drugs. This is most likely due to their widespread use and to their low therapeutic to toxic ratio. In spite of many improvements in anesthesia and post-operative care, pulmonary complications still occur in up to 50% of surgical patients and these complications are responsible for 20 to 25 percent of post-operative deaths. The incidence of pulmonary complications can be closely correlated with the anatomical site of surgery and its effect on the lung volumes and lung function. It has been shown that the incidence of pulmonary complication to be 35% after gastric or duodenal surgery, 15% after herniorrhaphy, and 1% peripheral surgery. The corresponding changes found in another study were 50.9±2.9% reduction in forced vital capacity and a decrease of 18.6±11.6 mm Hg in $P_4O_2$ after upper abdominal surgery. For lower adbominal surgery, the respective values were 24.4±18.1% and 9.5±10 mm Hg and for peripheral surgery 8.2±13.7% and 5.7±10 mm Hg.

Formerly, the hypoxia was thought to be caused by increased shunting for miliary atelectasis since often nothing could be seen on X-ray. However, it was shown that it was rather a disturbance in the matching of ventilation and perfusion in the lung. It has been found that patients with severe abdominal pain take spontaneous deep breaths, but these are much shallower than normal sighs. Morphine in the usual post-operative dosage suppresses the frequency of even these sub-normal sighs. With this reduction of lung volume and loss of sigh mechanism, it is obvious why so many develop atelectasis, collapse, pneumonia, and other complications.

The most effective means of dealing with this problem has been removal of the pain with block analgesia. Lung volumes and lung function improve and the need for narcotics is reduced or eliminated. This, in turn, leads to a reduction in post-operative pulmonary complications and length of hospital stay.

These differences are quite significant. For example, in one study the forced vital capacity (FVC) was 43.7±4.2% of the preoperative value in patients on narcotic analgesia following upper abdominal surgery. The comparable group who received a set of intercostal blocks had an FVC of 60.8±3.3%. The differences in blood gas changes were even more profound. The $P_4O_2$ dropped 11.1±3.1 mm Hg in the narcotic group but only 3.3±4.2 mm Hg in the block group. Of the 230 patients in this series, eleven had post-operative pulmonary complications. Nine of the eleven were receiving narcotics for analgesia. Thoracic epidural blocks give comparatively good results.

Metabolic response may also inhibit recovery from trauma and surgery. It consists of a marked catabolic response characterized by increased excretion of urinary nitrogen as a result of protein breakdown. This phenomenon is mediated by the central nervous and endocrine systems. For the response to occur, an intact afferent neural pathway is necessary. Previous studies have shown that afferent block by regional anesthesia will prevent the endocrine response to surgery, but the response occurs as the block subsides. This metabolic response may act to the patient's detriment. Blockade of the catabolic response seems to allow faster recovery with less morbidity.

The reason block techniques are not used more frequently is that with currently available local anesthetics, blocks cannot be sustained for more than twelve hours. In order to cover the period of high pain level after surgery, four to six sets of blocks are necessary and the quantity of skilled manpower for this kind of patient management is not routinely available. If an ultra-long acting local anesthetic were available, the blocks could conveniently be done at surgery. The resultant reduction in mortality, morbidity, and length of hospital stay would be extremely worthwhile.

Some local anesthetics appear to increase the absolute refractory period of the nerve with increasing frequency of transmission and this results in a frequency dependent or use-dependent inhibition. That is, a given dose of the drug produces more inhibition of the action potential as the frequency of impulses increases. The same anesthetics that show frequency dependent inhibition in vitro show clinically an increased sensory to motor dissociation of block, in agreement with the frequency coding of motor versus noxious sensory information.

The clinical importance of anesthetics with sensory/motor dissociation is most apparent in obstetrical analgesia where appropriate doses of local anesthetics with frequency dependent action (i.e., bupivicaine and lidocaine) provide freedom from pain while sparing enough motor function to allow participation in delivery. Sensory-motor discrimination will also be of great importance to the clinical efficacy of ultra-long acting local anesthetics. Whether it be for the treatment of chronic pain or long term postoperative analgesia new local anesthetics will have to offer the same block of noxious stimuli without loss of motor function and inocuous stimuli characteristic of the narcotic drugs presently in use for this purpose.

Thus, it can be seen that new and improved local anesthetics are highly desirable. Specifically, it would be desirable to have a local anesthetic that will give ultra-long (for instance, about three to 14 days) blockage of axonal conduction without causing any neural damage; that have a permanent charge to reduce or eliminate central nervous system toxicity and facilitate renal excretion; and that act primarily against sensory fibers (as opposed to motor).

SUMMARY OF THE INVENTION

The present invention provides a method for producing a long-lasting local anesthetic effect. The method comprises administering to a mammal an anesthetic producing amount of an N,N,N-triethyl-N-alkyl-ammonium salt wherein the alkyl group contains from 8 to about 16 carbon atoms.

It is surprising that these triethylalkyl quarternary ammonium salts produce a local anesthetic effect because they do not meet the requirements described by Lofgren which were thought necessary to produce such an effect. Indeed the local anesthetic compounds of the present invention have no carbonyl group, no aromatic group and the amino group is a quaternary ammonium rather than the usual tertiary amine having a pKa in the physiologic range.

The quaternary ammonium salts useful in this invention provide a surprisingly long-lasting local anesthetic effect, i.e. up to 20 days or more. The duration of the local anesthetic effect varies with the length of the alkyl group. Straight chain alkyl groups are preferred for the quaternary salts used in the practice of this invention.

The quaternary ammonium local anesthetics of this invention do not appear to act as neurolytic agents but appear to block axonal conduction by interfering in some fashion with the function of the axonal membrane. These compounds have little apparent neurotoxicity, and less systemic toxicity than conventional tertiary amine local anesthetics.

DETAILED DESCRIPTION OF THE INVENTION

Figure 1:
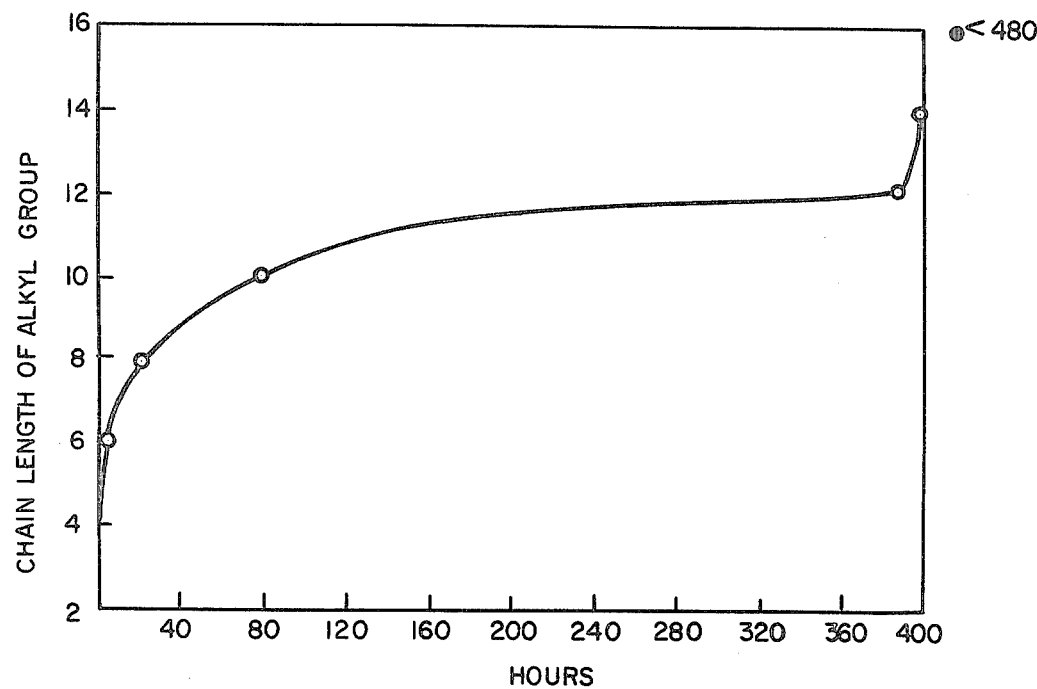
FIG. 1 is a graph illustrating the duration of local anesthetic effect vs. alkyl carbon chain length for the quaternary ammonium compounds of this invention.

In accord with the present invention long-lasting local anesthetic compounds are provided. The compounds are quaternary ammonium compounds having the following structure:

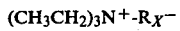
(I)

wherein R is an alkyl group having from about 8 to about 16 carbon atoms, preferably 8 to 12 carbon atoms and $X^-$ is a suitable pharmacological anion. The alkyl group is preferably a normal alkyl group. Suitable alkyl groups include, for instance, octyl, nonyl, decyl, undecyl, dodecyl, tridecyl, tetradecyl, pentadecyl, and hexadecyl, as well as substituted such groups.

The quaternary ammonium compounds used in this invention are readily prepared by standard chemical procedures. For example, triethyl amine and the appropriate bromoalkane are combined in a 1:1 molar ration with excess acetone. The acetone is driven off at 60° C. for about two hours and the desired quaternary salt crystallized by immersion in ice water. The resulting product is then washed with petroleum ether on filter paper to remove unreacted starting materials. Purity is tested by thin layer chromatography.

In use, the quaternary ammonium compound can be administered by a variety of techniques such as, for example, by injection, by topical application, or by suppository, etc. The compound is conveniently formulated with a suitable pharmacological carrier dependent upon the desired administrated route. For instance, for injection, the carrier is conveniently physiological saline solution. For topical use, the compound is conveniently formulated into a cream or ointment, etc.

The administered dose depends upon many criteria, including the site for the desired effect, the route of administration, the particular local anesthetic used, its toxicity and its half-life, the medical problem being treated, etc. When injecting a composition of the compound in normal saline onto the nerve, a dose of from 1 mg to 5 mg in 0.2 ml saline has been found effective for obtaining localized anesthetic effect.

The invention will now be further illustrated by the following examples.

EXAMPLES 1-7

Tetraethylammonium bromide ($C_2$) was obtained from Aldrich Chemical Co. Compounds of formula I wherein R is a six carbon chain length alkyl group ($C_6$), an eight carbon alkyl group ($C_8$), ten ($C_{10}$), twelve ($C_{12}$), fourteen ($C_{14}$) and sixteen ($C_{16}$) carbon alkyl groups, respectively were prepared as the bromide salt by the synthesis described previously. Bromoalkanes having varying carbon chain lengths and triethylamine are readily available and were purchased from commercial sources such as, for example, Eastman Organic Chemicals, Aldrich Chemical Co., and Sigma Chemical Co.

Male Sprague-Dawley rats were obtained having a 300-400 g body weight. After light ether anesthesia the rats were injected with 10 mg of sodium pentobarbital, I.P., and then given additional pentobarbital, if necessary, until the animal lost righting reflex and allowed injection of the test compounds. 1.0 and 5.0 mg of each compound in 0.2 ml of normal saline was injected onto the trigeminal nerve through a 30 gauge needle guided to the nerve by a metal jig positioned on the roof of the mouth by the incisors and molars. The contralateral trigeminal nerve was used as a control throughout the experiment. Anesthesia was tested by stimulating the lip/whisker area innervated by the maxillary nerve on experimental and control sides and observing whether the stimulus produced a reflex contraction of abdominal muscles (unanesthetized) or not (anesthetized). Stimulation consisted of 1-10 V 6 msec square wave pulse trains (2 pulses/sec for 5 sec) produced by a Grass S48 stimulator triggering a stimulus isolation unit (DS-2, Digitimer Ltd.), and were delivered through bipolar electrodes (two 30 gauge needles 2 mm apart). The muscle twitch response was quantitated by recording the EMG from muscle of the abdoiminal wall, and displaying it on a Tektronic 5111 oscilloscope after amplification (Tektronic AM502 differential amplifier). Comparison of the EMG response produced by stimulating the control and treated side allowed an accurate determination of the presence or absence of trigeminal nerve block.

The time required for the onset of nerve blocking (anesthesia) and the total period for which nerve blocking was provided is tabulated below in Table 1 and the blocking duration versus chain length of R is plotted in FIG. 1.

TABLE 1

| Example No. | R | No. of Animals | Dose | Onset of Block (min)$^a$ | Duration of Block (hrs)$^a$ |
|---|---|---|---|---|---|
| 1 | $C_2$ | 4 | 5.0 mg | 19 ± 2 | 1.2 ± 1.6 |
| 2 | $C_6$ | 4 | 2.5 mg | 18 ± 6 | 6 ± 1 |
| 3 | $C_8$ | 4 | 1.7 mg | 10 ± 5 | 21 ± 2 |
| 4 | $C_{10}$ | 4 | 2.0 mg | 6 ± 3 | 80 ± 8 |
| 5 | $C_{12}$ | 5 | 1.0 mg | 3 ± 2 | 388 ± 96 |
| 6 | $C_{14}$ | 4 | 1.0 mg | 11 ± 6 | 402 ± 72 |
| 7 | $C_{16}$ | 4 | 2.3 mg | 24 ± 7 | 480 ± 96 |

$^a$mean ± S.D.

EXAMPLE 8

Carbon 14 labeled $C_{12}$ (Ethyl-1-$^{14}$C, N,N,N-triethyl-N-dodecyl ammonium bromide) was used to determine the binding of $C_{12}$ to the infraorbital nerve, and its mode of excretion, rats were injected with a blocking dose of $C_{12}$ containing 0.5 $\mu$Ci of $^{14}$C, and placed in an animal metabolism unit. Feces and urine were collected daily. Feces were dissolved in Soluene 350 at 50° C. and after decolorization with hydrogen peroxide and isopropyl alcohol, were counted in Dimilume 30 liquid scintillation cocktail (Packard Instruments); urine was added directly to cocktail. At the end of the binding experiments, rats were sacrificed and the infraorbital nerve dissected free, washed, divided into five 5 mm sections, and dissolved in Soluene prior to counting in Dimilume on a Packard PRIAS LSC.

The infraorbital nerve was dissected from the treated animals 7–10 days after injection and fixed in Karnovsky's fixative (1% paraformaldehyde, 1% gluteraldehyde in 0.1 M Na-cacodylate buffer pH 7.4) overnight, post-fixed in osmium, dehydrated in alcohol, and embedded in Epon prior to sectioning.

Figure 2:
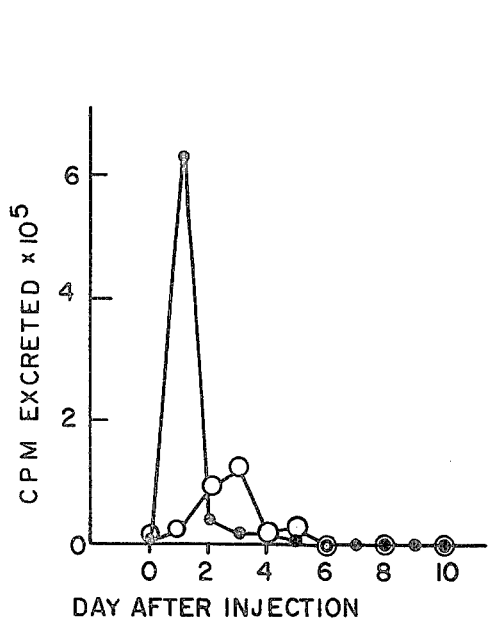
FIG. 2 is a graph illustrating the concentration of N,N,N-triethyl-N-dodecyl ammonium bromide in the nerve and in excretions at various times after injection.
Figure 3:
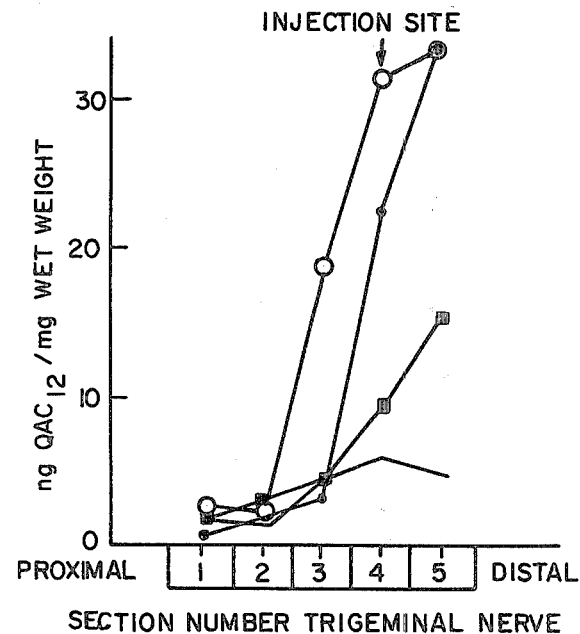
FIG. 3 is a graph illustrating the concentration of N,N,N-triethyl-N-dodecyl ammonium bromide in the rat infra-orbital nerve at various times after injection.

FIG. 2 shows the concentration of anesthetic in the nerve and excreted in the feces of the rats at various times after injection. FIG. 3 illustrates the concentration of anesthetic in the infraorbital nerve at various times after injection. All points in the figures represent the mean data from three rats.

Electron micrographs of 20 to 30 myelinated and unmyelinated axons from three $C_{12}$ treated and three control infraorbital nerves were evaluated for axonal swelling, myelin ultrastructure and general integrity on a 1–5 scale. No obvious ultrastructural damage was observed on the treated nerves.

The invention has been described in detail with reference to the preferred embodiments thereof. However, it will be appreciated that those skilled in the art, upon reading this disclosure, may make modifications and improvements within the spirit and scope of the invention.

We claim:

1. A method for providing a local anesthetic effect, said method comprising administering to a mammal a local anesthetic effect producing amount of an N,N,N-triethyl-N-alkyl ammonium salt wherein the alkyl group contains from about 8 to about 16 carbon atoms.

2. The method of claim 1 wherein said alkyl group contains from about 8 to about 12 carbon atoms.

3. The method of claim 1 wherein the alkyl group is a normal alkyl group.

4. The method of claim 1 wherein said ammonium salt is N,N,N-triethyl-N-dodecyl ammonium bromide.

5. The method of claim 1 wherein said ammonium salt is N,N,N-triethyl-N-octyl ammonium bromide.

6. The method of claim 1 wherein said ammonium salt is N,N,N-triethyl-N-decyl ammonium bromide.

7. The method of claim 1 wherein said ammonium salt is N,N,N-triethyl-N-hexadecyl ammonium bromide.

8. The method of claim 1 wherein said ammonium salt is N,N,N-triethyl-N-tetradecyl ammonium bromide.

* * * * *